United States Patent [19]

Reese

[11] Patent Number: 4,903,692

[45] Date of Patent: Feb. 27, 1990

[54] BONE CLAMP INSTALLATION TOOL

[76] Inventor: Hewitt W. Reese, 1940 E. Southern Ave., Tempe, Ariz. 85282

[21] Appl. No.: 348,593

[22] Filed: May 8, 1989

[51] Int. Cl.$^4$ .............................................. A61F 5/04
[52] U.S. Cl. ...................................... 606/99; 606/104
[58] Field of Search ............. 128/92 R, 92 Y, 92 YE, 128/92 V, 92 VZ, 92 VT, 303 R, 334 R, 334 C

[56] References Cited

U.S. PATENT DOCUMENTS

| | | | |
|---|---|---|---|
| 2,485,531 | 10/1949 | Dzus | 128/92 YF |
| 4,326,531 | 4/1982 | Shimonaka | 128/326 |
| 4,531,517 | 7/1985 | Forte | 128/92 VT |
| 4,614,187 | 9/1986 | Mulhollan | 128/303 R |
| 4,688,561 | 8/1987 | Reese | 128/92 YF |
| 4,796,612 | 1/1989 | Reese | 128/92 YF |

Primary Examiner—Richard J. Johnson
Attorney, Agent, or Firm—Harry M. Weiss

[57] ABSTRACT

A syringe-like bone clamp installation tool has a hollow piston with a longitudinal slot. A shank end of a Reese clamp and at least one of a plurality of right truncated cones of a central portion thereof are disposed within the piston. The piston is slidably disposed within a hollow barrel that has a proximal end from which a forked tab extends through the slot into the piston. The tines of the fork maintain the cone against motion relative to the barrel. An open end is the piston is countersunk to receive a button of the clamp exterior to the piston. As the barrel is moved towards the closed end of the piston, the button is advanced.

6 Claims, 1 Drawing Sheet

U.S. Patent
Feb. 27, 1990
4,903,692
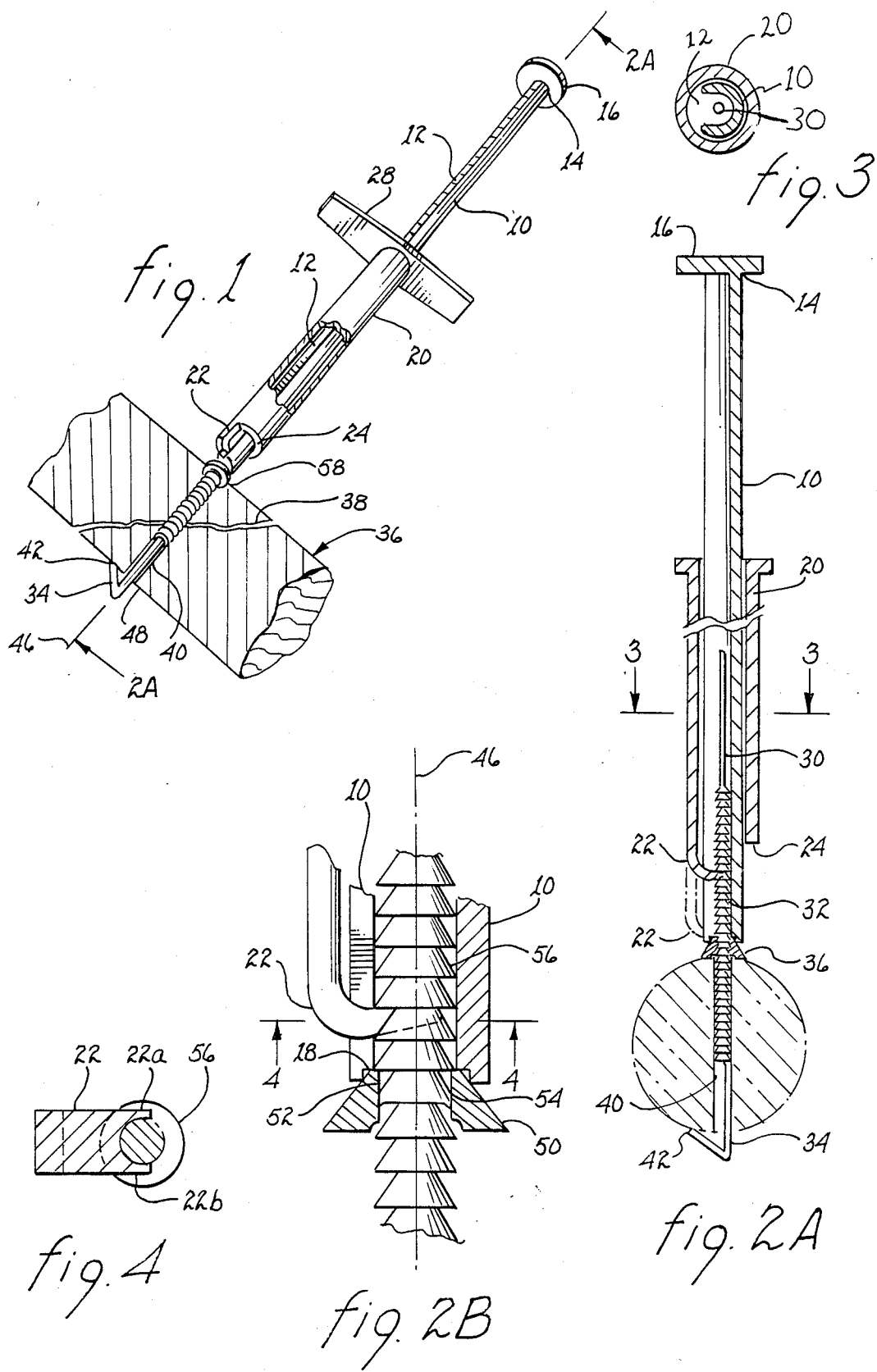

BONE CLAMP INSTALLATION TOOL

BACKGROUND OF THE INVENTION

1. Field of the Invention

This invention relates to tools for installing clamps to repair a bone fracture and methods therefore and, more particularly, to a tool for installing a clamp of the type that is threaded through a hole drilled through a fractured bone, and method therefore.

2. Description of the Prior Art

One treatment procedure for a fractured bone is to drill a hole therethrough that intersects the fracture. The hole is used for installation of a type of clamp which applies a force that holds the fractured bone together. A clamp of this type is disclosed in U.S. Pat. No. 4,796,612 of Hewitt W. Reese (referred to hereinafter as a Reese clamp) which is hereby incorporated herein and made a part hereof.

The Reese clamp is made of an elastically deformable material molded to form a hook and a shank, at respective ends thereof. The central portion of the Reese clamp is comprised of a plurality of similar right truncated cones that are coaxially disposed, with the base of one cone connected to the top of an adjacent cone. The cones are oriented with their bases towards the hook end.

The Reese clamp additionally includes a button having a central hole therethrough. The diameter of the hole through the button is intermediate to the diameters of the base and the top of the cones. The button is disposed upon the central portion, a portion of a cone thereof being within the central hole.

Because of the diameter of the button, the orientation of the cones and the elastic deformability of the material, the button and the central portion form a pawl and ratchet, respectively, where the button may be advanced towards the hook end, but not towards the shank end.

The hook may be elastically deformed from its original shape and threaded through the drilled hole. When threaded through, the hook to resumes its original shape.

The threaded through hook bears against a distal cortex of the bone in much the same way a toggle bolt bears against an interior surface of a wall. The button is thereafter advanced to bear against a proximal cortex of the bone, thereby holding the fractured bone together.

Although the Reese clamp has proven utility, there is a need for a simple, reliable, economic tool for installing the Reese clamp.

SUMMARY OF THE INVENTION

An object of the present invention is to provide an apparatus and a method for installing a clamp that holds a fractured bone together.

Another object of the present invention is to provide an apparatus and method for installing a Reese clamp.

Another object of the present invention is an apparatus and method for maintaining a shank end of a Reese clamp against movement with respect to a fractured bone while the button thereof is advanced to hold the fractured bone together.

Another object of the present invention is an apparatus and method for advancing the button of a Reese clamp.

According to the present invention, a hollow piston with a longitudinal slot is within a hollow barrel that has a tab that extends within the slot. When a shank end and at least one cone of a plurality of cones of the central portion of a Reese clamp are disposed within the piston, the tab maintains the one cone against motion relative to the barrel. The open end of the piston is moveable against the button of the clamp towards a hook end thereof.

An installation tool of the present invention is especially suited for use with a Reese clamp. Additionally, the tool is simple, reliable and economic to construct.

These and other objects, features and advantages of the present invention, as well as details of the preferred embodiment thereof, will be more fully understood from the following description and drawing.

BRIEF DESCRIPTION OF THE DRAWING

FIG. 1 is a perspective view, with parts broken away, of the preferred embodiment of the present invention;

FIG. 2A is a view of the embodiment of FIG. 1 taken along the line 2A—2A;

FIG. 2B is a partial side elevation, with parts broken away, of the embodiment of FIG. 1;

FIG. 3 is a view of the embodiment, as shown in FIG. 2A, taken along the line 3—3; and FIG. 4 is a view of the embodiment, as shown in FIG. 2B, taken along the line 4—4.

DESCRIPTION OF THE PREFERRED EMBODIMENT

As shown in FIGS. 1, 2A and 3, a syringe-like clamp installation tool is comprised of a hollow piston 10 that has a longitudinal slot 12. A closed end 14 of piston 10 is integrally connected to a disc shaped plunger knob 16.

As shown in FIG. 2B, piston 10 has an open end 18 that is preferably countersunk. As explained hereinafter, a button of a Reese clamp is seated against end 18.

A portion of piston 10 is slidably disposed within a hollow barrel 20 (FIGS. 1 and 2A). An essential feature of the installation tool is a tab 22 (FIGS. 1 and 2B) that is integrally connected to an end 24 of barrel 20. Additionally, tab 22 extends through slot 12 into piston 10. Tab 22 preferably has a forked end. As explained hereinafter, tab 22 maintains a cone of a central portion of a Reese clamp against motion relative to barrel 20 as the button of the clamp is advanced.

Barrel 20 has an open end 26 integrally connected to bosses 28. In a manner similar to a syringe, bosses 28 are used in conjunction with knob 16 to slide piston 10 within barrel 20.

Piston 10 has disposed therein a shank 30 of a Reese clamp (FIG. 2A). Shank 30 is connected to one end of a central portion 32 of the clamp; the other end of central portion 32 is connected to a hook 34. Shank 30, central portion 21 and hook 34 are made in a mold from an elastically deformable material.

Central portion 32 is comprised of a plurality of right truncated cones that are coaxially connected. Moreover, the cones and oriented with their bases towards hook 34.

When the Reese clamp is used to repair a bone 36 (FIGS. 1 and 2A) that has a fracture 38, a hole 40 is drilled to intersect fracture 38. The diameter of hole 40 is less than the distance from an end 42 of hook 34 to a central axis 46 of the Reese clamp.

Hook 34 is elastically deformed and threaded through hole 40. When hook 34 is threaded through, it resumes its original shape, whereby end 42 bears against a distal cortex 48 of bone 36 in much the same way a toggle bolt bears against an interior surface of a wall.

The Reese clamp additionally includes a button 50 that has a central hole 52 therethrough (FIG. 2B). Hole 52 has a diameter intermediate to the diameters of the base and the top of the cones. Button 50 is mounted on central portion 32 with a cone 54 thereof within hole 52. Because of the diameter of hole 52, cone 54 is deformed.

It should be understood that because of the orientation of the cones and the diameter of hole 52, button 50 and central portion 32 form a pawl and a ratchet, respectively. Accordingly, button 50 is moveable towards hook 34 but not moveable towards shank 30.

As shown in FIG. 4, tines 22a and 22b of tab 22 bear against the base of a cone 56 of central portion 32. Therefore, when knob 16 is moved towards bosses 28, tab 22 maintains cone 56 against motion relative to barrel 20. Additionally, button 50 is seated within end 18. Therefore, the movement of knob 16 causes button 50 to advance towards hook 34. Button 50 is advanced until it bears against a proximal cortex 58 of bone 36, whereby bone 36 is held together.

It should be understood that when button 50 bears against cortex 58, a tension stress is imposed upon hook 34 and central portion 32. Preferably, tab 22 is of lesser structural strength than hook 34 and central portion 32. The lesser structural strength is a safety factor that causes tab 22 to break prior to a possible breakage of hook 34 or central portion 32 due to the tension stress.

While the invention has been particularly shown and described with respect to a preferred embodiment thereof, it will be understood by those skilled in the art that changes in form and detail may be made therein without departing from the spirit and the scope of the invention.

I claim:

1. A bone clamp installation tool, comprising:
a hollow barrel;
a hollow piston having a longitudinal slot at least at the lower end thereof, said piston having disposed therein a shank end and at least one of a plurality of truncated cones of a bone clamp, said bone clamp having a locking button thereon engagable with successive cones that is seated against an open end of said piston, said piston being manually adjustably slideably disposed within said barrel; and
means on said barrel positioned in said slot for engaging said at least one cone to cause motion of said shank relative to said button.

2. The tool of claim 1 wherein said engaging means comprises a tab that is connected to an open end of said barrel, said tab extending through said slot into said piston and being adapted to fit against the base of said one cone.

3. The tool of claim 2 wherein said tab has a forked end that fits against said base.

4. The tool of claim 2 wherein said tab is integrally connected to said barrel.

5. The tool of claim 2 wherein said tab is of lesser structural strength than a hook and a cenural portion of said bone clamp.

6. The tool of claim 1 wherein said open end of said piston is countersunk.

* * * * *

UNITED STATES PATENT AND TRADEMARK OFFICE
CERTIFICATE OF CORRECTION

PATENT NO. : 4,903,692

DATED : February 27, 1990

INVENTOR(S) : Hewitt W. Reese

It is certified that error appears in the above-identified patent and that said Letters Patent is hereby corrected as shown below:

In column 4, Claim 5, line 29, please change "cenural" to --central--.

Signed and Sealed this

Twelfth Day of November, 1991

Attest:

HARRY F. MANBECK, JR.

Attesting Officer

Commissioner of Patents and Trademarks